(12) United States Patent
Kubin (10) Patent No.: US 11,234,957 B2
(45) Date of Patent: Feb. 1, 2022

(54) PROCESS FOR PREPARING WATER SOLUBLE FORSKOLIN

(71) Applicant: SciPharm S.à.r.l., Mertert (LU)

(72) Inventor: Andreas Kubin, Eichengraben (AT)

(73) Assignee: SciPharm S.à.r.l, Mertert (LU)

( * ) Notice: Subject to any disclaimer, the term of this patent is extended or adjusted under 35 U.S.C. 154(b) by 215 days.

(21) Appl. No.: 16/476,337

(22) PCT Filed: Jan. 9, 2018

(86) PCT No.: PCT/EP2018/050447
§ 371 (c)(1),
(2) Date: Jul. 8, 2019

(87) PCT Pub. No.: WO2018/127600
PCT Pub. Date: Jul. 12, 2018

(65) Prior Publication Data
US 2021/0145791 A1    May 20, 2021

(30) Foreign Application Priority Data
Jan. 9, 2017 (EP) ..................... 17150644

(51) Int. Cl.
*A61K 31/352* (2006.01)
*A61K 47/40* (2006.01)
*A61K 9/08* (2006.01)

(52) U.S. Cl.
CPC .............. *A61K 31/352* (2013.01); *A61K 9/08* (2013.01); *A61K 47/40* (2013.01)

(58) Field of Classification Search
CPC ......... A61K 31/352; A61K 9/08; A61K 47/40
USPC ...................................................... 514/455
See application file for complete search history.

(56) References Cited

U.S. PATENT DOCUMENTS

| 4,826,963 | A  | 5/1989  | Stadler née Szoke et al. |
| 6,960,300 | B2 | 11/2005 | Majeed et al. |
| 2005/0051483 | A1 | 3/2005 | Muhammed et al. |

FOREIGN PATENT DOCUMENTS

| JP | S 62-103077 A | 5/1987 |
| JP | H 05-051375 A | 3/1993 |
| JP | 2001-510810 A | 8/2001 |
| JP | 2007-505040 A | 3/2007 |
| JP | 2010-270100 A | 12/2010 |
| WO | WO 1999/004823 | 2/1999 |
| WO | WO 2005/025500 | 3/2005 |

OTHER PUBLICATIONS

Gupta et al., "Dual-drug delivery system based on in situ gel-forming nanosuspension of forskolin to enhance antiglaucoma efficacy," *AAPS PharmaSciTech*, 11(1):322-335, 2010.
Office Communication issued in Indian Patent Application No. 201927032001, dated Feb. 24, 2021.
Extended European Search Report issued in European Patent Application No. 17150644.7, dated Jul. 17, 2016.
Huang et al., "Inhibition of forskolin-activated adenylate cyclase by ethanol and other solvents," *J. Cyclic. Nucleotide Res.*, 8(6):385-394, 1982.
Hussain et al., "Treprostinil stimulates the engraftment of haematopoetic stem cells," *BMC Pharmacology*, 11(Suppl. 2):A6, 2011.
Ito et al., "Effects of a water-soluble forskolin derivative (NKH477) and a membrane-permeable cyclic AMP analogue on noradrenaline-induced Ca2+ mobilization in smooth muscle of rabbit mesenteric artery," *Br. J. Pharmacol.*, 110(3):1117-1125, 1993.
Laurenza et al., "Stimulation of adenylate cyclase by water-soluble analogues of forskolin," *Molecular Pharmacology*, 32(1):133-139, 1987.
Li et al., "A forskolin derivative, FSK88, induces apoptosis in human gastric cancer BGC823 cells through caspase activation involving regulation of Bcl-2 family gene expression, dissipation of mitochondrial membrane potential and cytochrome c release," *Cell Biol. Intern.*, 30(11):940-946, 2006.
Loftsson et al., "Cyclodextrins in drug delivery," *Expert Opinion on Drug Delivery*, 2(2):335-351, 2005.
Metzger et al., "The positive inotropic-acting forskolin, a potent adenylate cyclase activator," *Arzneimittelforschung*, 31(8):1248-1250, 1981.
PCT International Preliminary Report on Patentability issued in International Application No. PCT/EP2018/050447, dated Jul. 9, 2019.
PCT International Search Report and Written Opinion issued in International Application No. PCT/EP2018/050447, dated Feb. 28, 2018.
Saettone et al., "Preparation and evaluation in rabbits of topical solutions containing forskolin," *Journal of Ocular Pharmacology*, 5(2):111-118, 1989.
English translation of Office Communication issued in Japanese Patent Application No. 2019-537301, dated Oct. 12, 2021.
Sonnendecker et al., "Large-ring cyclodextrins as chiral selectors for enantiomeric pharmaceuticals," *Angew Chem. Int. E.d Engl*, 58:5411-6414, 2019.

*Primary Examiner* — Kristin A Vajda
(74) *Attorney, Agent, or Firm* — Parker Highlander PLLC (57) ABSTRACT

The invention relates to a new method for preparing a complex of forskolin and cyclodextrin and inclusion complexes of forskolin and γ-cyclodextrins having a weight ratio of 1:0.2 to 1:4 (w/w). Pharmaceutical compositions comprising said complex and their use are also provided.

14 Claims, 4 Drawing Sheets

PROCESS FOR PREPARING WATER SOLUBLE FORSKOLIN

This application is a national phase application under 35 U.S.C. § 371 of International Application No. PCT/EP2018/050447, filed Jan. 9, 2018, which claims the benefit of European Patent Application No. 17150644.7, filed Jan. 9, 2017; the entirety of each aforementioned disclosure is incorporated herein by reference.

The invention relates to a new method for preparing a complex of forskolin and cyclodextrin and inclusion complexes of forskolin and γ-cyclodextrins having a weight ratio of 1:0.2 to 1:4 (w/w). Pharmaceutical compositions comprising said complex and their use are also provided.

BACKGROUND OF THE INVENTION

Forskolin is a labdane diterpene that is produced by the Indian *Coleus forskolii* plant (*Plectranthus barbatus*). Forskolin is commonly used as a tool in biochemistry to raise levels of cyclic AMP (cAMP) in the study and research of cell physiology. Forskolin activates the enzyme adenylyl cyclase and increases intracellular levels of cAMP (Metzger H. et al., 1981, Arzneimittelforschung, 1248-50). cAMP is an important second messenger necessary for the proper biological response of cells to hormones and other extracellular signals. It is required for cell communication in the hypothalamus/pituitary gland axis and for the feedback control of hormones. Cyclic AMP acts by activating cAMP-sensitive pathways such as protein kinase A and Epac.

Forskolin is a diterpene containing 2α-hydroxyl groups at the 1- and 9-positions, a ß-hydroxyl group at the 6-position and a ß-acetoxy group at the 7-position with limited water solubility thus making it difficult to analyze forskolin activation curves and to use it for drug development. Organic solvents have been shown to solubilize forskolin, however, said solvents can also inhibit the ability of forskolin to activate adenylate cyclase (Huang R. D. et al., 1982, J. Cyclic. Nucleotide Res., 385-394).

Aqueous solutions of forskolin had also been produced by dissolving forskolin in solutions of hydroxypropyl-γ-cyclodextrin. Maximum solubility of forskolin was 2.5 mM and 9.8 mM in 40% (w/v) aqueous solutions of hydroxypropyl-ß-cyclodextrin and hydroxypropyl-γ-cyclodextrin, respectively (Laurenza A. et al., 1987, Molecular Pharmacology, 32:133-139). Thereby an increase of solubility of approx. 16-fold and approx. 65-fold was received.

Cyclodextrins are a family of cyclic oligosaccharides with a hydrophilic outer surface and a lipophilic central cavity. They consist of (α-1,4)-linked α-D-glucopyranose units with a lipophilic central cavity. Due to the chair formation of the glucopyranose units, cyclodextrin molecules are shaped like cones with secondary hydroxyl groups extending from the wider edge and the primary groups from the narrow edge. Cyclodextrins are relatively large with a number of hydrogen donors and acceptors and do not permeate lipophilic membranes.

In pharmaceutical industry cyclodextrins have mainly been used as complexing agents to increase aqueous solubility of poorly soluble drugs, and to increase their bioavailability and stability (Loftsson T., et al., 2005, Expert. Opin. Drug Deliv., 335-351).

The most common natural cyclodextrins consist of six (α-cyclodextrin), seven (ß-cyclodextrin) and eight (γ-cyclodextrin) glucopyranose units. Further known natural cyclodextrins are δ cyclodextrins. Random substitution of the hydroxyl groups can result in increased solubility. The main reason for solubility enhancement is that random substitution transforms the crystalline cyclodextrins into amorphous mixtures of isomeric derivatives. Cyclodextrin derivatives include hydroxypropyl derivatives of ß- and γ-cyclodextrin, the randomly methylated ß-cyclodextrin, sulfobutylether ß-cyclodextrin and branched cyclodextrins such as glucosyl-ß-cyclodextrin (Loftsson T. et al., 2005). On reacting cyclodextrin in alkaline solution with propylene oxide a 2-hydroxypropyl group will be connected to one or more hydroxyls of the cyclodextrin (HP-cyclodextrin). A higher substitution of the hydroxyls with 2-hydroxypropyl also results in the formation of oligomeric hydroxypropylene oxide side chain formation.

Various methods for preparing drug-cyclodextrin complexes are already known, such as for example, co-precipitation, slurrying, kneading or grinding. In US20050051483, a forskolin ß-cyclodextrin complex is produced by adding forskolin to water containing dissolved hydroxypropyl-ß-cyclodextrin, agitating the mixture and filtering it.

Saettone M. F. et al. describe topical solutions containing forskolin. It is specifically stated that ß- and γ-cyclodextrins were not effective solubilizers of forskolin (Journal of Ocular Pharmacol, vol. 5, no. 2, 1989, pp. 111-118)

However, there is still a need for providing improved methods for complexing forskolin with cyclodextrin leading to cyclodextrin-complexes with high content of forskolin.

The object of the present invention is to provide a method for improved complexing of cyclodextrin and forskolin and to provide a forskolin complex with improved solubility but preserved structure.

SUMMARY OF THE INVENTION

The object is solved by the embodiments of the present invention.

According to the invention there is provided an inclusion complex comprising forskolin and γ-cyclodextrin in a weight ratio of 1:0.2 to 1:4 (w/w), wherein forskolin and γ-cyclodextrin are comprised as an aqueous soluble complex.

According to a specific embodiment, the γ-cyclodextrin is hydroxypropyl-γ-cyclodextrin.

According to an embodiment of the invention, the weight ratio of forskolin and hydroxypropyl-γ-cyclodextrin is in the range of about 1:0.5 to 1:3.3 (w/w).

In an alternative embodiment, about 2.5-4.5 mg, specifically about 3 to 4 mg forskolin are present in 100 mg forskolin-cyclodextrin complex. Specifically about 2.5%, specifically about 3%, specifically about 3.5%, specifically about 3.7%, specifically about 4%, specifically about 4.5% (w/w), more specifically more than 5% (w/w) forskolin are present in the inclusion complex of the invention.

It was surprisingly shown that complexing of forskolin with cyclodextrin highly improves the solubility in water. Forskolin cyclodextrin complex has approximately about 100 times, specifically about 120 times the solubility of native forskolin. It was also surprisingly shown that the native structure of forskolin is preserved when complexed with cyclodextrin and that the activation potential of forskolin for adenylyl cyclase is also preserved thus complexation with cyclodextrins does not reduce the activation.

In another embodiment, the invention provides an administration formulation comprising an inclusion complex of the present invention together with suitable pharmaceutical auxiliaries.

In a further embodiment, a pharmaceutical composition comprising the inventive forskolin cyclodextrin inclusion complex, optionally together with further excipients, is provided.

In embodiments, the invention additionally provides a method of treating or preventing a condition treatable or preventable with forskolin, comprising administering to a subject in need of such treatment or prevention a pharmaceutically acceptable effective amount of a stable inclusion complex comprising forskolin and a cyclodextrin, specifically hydroxypropyl-γ-cyclodextrin.

The present invention provides a method for preparing a forskolin cyclodextrin inclusion complex comprising the steps:

a) mixing forskolin and cyclodextrin in a weight ratio of 1:0.5 to 1:4, b) adding water and solvent to form a pasty mixture, c) heating said mixture up to a temperature ranging from 200° C. to 230° C., specifically to about 220° C., d) adding water to said mixture followed by mixing and allowing the mixture to precipitate, e) isolating the precipitate from the mixture and optionally drying the precipitate.

In a specific embodiment, the cyclodextrin used in the method is selected from the group consisting of α-cyclodextrin, hydroxypropyl-α-cyclodextrin (HP-α-CD), ß-cyclodextrin, hydroxypropyl-ß-cyclodextrin (HP-ß-CD), γ-cyclodextrin, hydroxypropyl-γ-cyclodextrin (HP-γ-CD), delta (δ)-cyclodextrin, hydroxypropyl-δ-cyclodextrin (HP-δ-CD) and randomly methylated-ß-cyclodextrin (RAMEB-CD).

HP-ß-CD, RAMEB-CD, and HP-γ-CD provide significantly increased occupancy rates and are specifically used in the method described herein.

Specifically, the heating temperature used in the method is about 220° C.

According to an embodiment of the invention, the method is used for producing a powdered inclusion complex of forskolin and HP-γ-cyclodextrin.

In a specific embodiment, the solvent used in the present invention is an alcohol, specifically it is 2-propanol.

According to an embodiment, the precipitate is heat dried, specifically the drying step is carried out for about 1 to 30 minutes.

According to a further embodiment, the precipitate is filtered, specifically by membrane filtration and optionally the precipitate is dried.

DETAILED DESCRIPTION

Specific terms as used throughout the specification have the following meaning.

The term "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

According to the present invention the term "complex" denotes an inclusion body complex, a non-inclusion body complex, a co-precipitate or a lyophilized complex. Preferably, it is a lyophilized complex or an inclusion complex.

Figure 1:
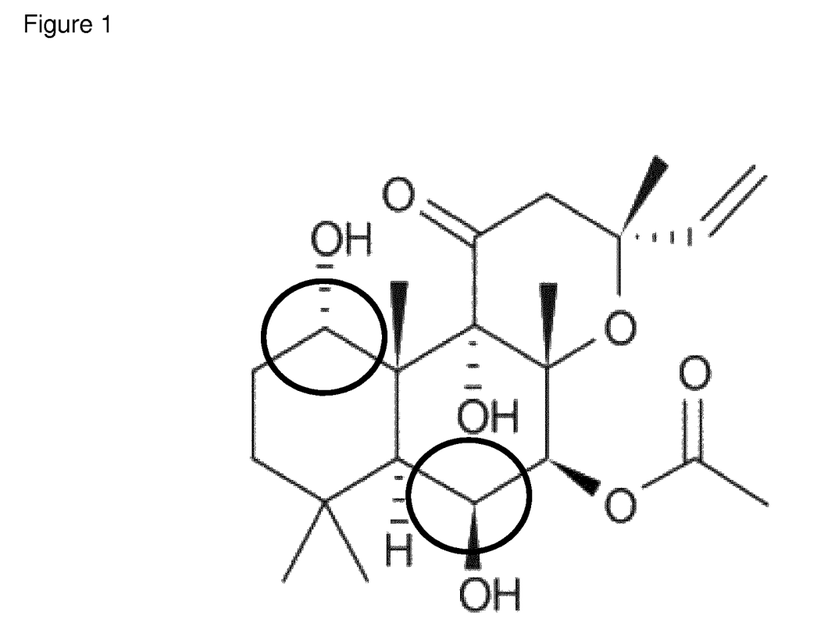
FIG. 1: Structure of forskolin and binding sites to the C1 and C2 domain of adenylyl cyclase. The two OH-groups (marked with cycles) are essential for binding and must not be derivatized for these applications.

Forskolin (Colforsin; 7-beta-acetoxy-8,13-epoxy-1-alpha, 6-beta, 9-alpha-trihydroxylabd-14-en-11-one; Coleonol) has the molecular formula $C_{22}H_{34}O_7$ and is of the structure as shown in FIG. 1.

As referred herein, the term "forskolin" also encompasses any congeners, analogs or derivatives of forskolin of natural or synthetic origin, which can be, but not limited to, isoforskolin, 7-deacetylforskolin, colforsin daropate hydrochloride, NKH477 (Ito S. et al., 1993, Br. J. Pharmacol. 110(3), 1117-25), FSK88 (Zhonghai L. et al., 2006, Cell Biol. Intern., 30(11), 940-946).

As used herein, the term "cyclodextrin" refers to a cyclic dextrin molecule that is formed by enzyme conversion of starch. Cyclodextrins are cyclic oligosaccharides. The cyclodextrins can be α-cyclodextrin, composed of a ring of six glucose residues; β-cyclodextrin, composed of a ring of seven glucose residues; γ-cyclodextrin, composed of a ring of eight glucose units and δ-cyclodextrin. The inside cavity of a cyclodextrin is lipophilic, while the outside of the cyclodextrin is hydrophilic. β-cyclodextrin is not known to have any toxic effects, is World-Wide GRAS (i.e., Generally Regarded As Safe), natural, and is FDA approved. α-cyclodextrin and γ-cyclodextrin are also considered natural products and are U.S. and E.U. GRAS. α-, β- or γ-cyclodextrins prepared by the enzymatic conversion of starch differ in the diameter of their hydrophobic cavity and are generally suitable for inclusion of numerous lipophilic substances. The use of cyclodextrins as excipients is also allowed by the European Medicines Agency (Background review for cyclodextrins used as excipients, November 2014, EMA/CHMP/333892/2013).

A method for preparing a forskolin cyclodextrin inclusion complex is encompassed herein comprising the sequential steps of:

a) mixing forskolin and cyclodextrin in a weight ratio of 1:1 to 1:1.5, b) adding water to form a pasty mixture, c) adding a solvent to said mixture, d) heating said mixture at a temperature ranging from 200° C. to 230° C., specifically ranging from 210° C. to 225° C., specifically ranging from 215° C. to 225° C. more specifically at about 220° C., e) adding water to said mixture followed by mixing and allowing the mixture to precipitate, f) isolating the precipitate from the mixture and optionally drying the precipitate.

In other embodiments, solvent and water are simultaneously added to cyclodextrin and forskolin or the solvent can also be added before water is given to forskolin and cyclodextrin.

Solvents can be any organic or anorganic solvents like, but not limited to, alcohols, acetone, dichlormethane etc. Alcohols are known to be useful solvents, specifically secondary alcohols like isopropyl alcohol (2-propanol), cyclohexanol. As an alternative, also primary alcohols can be used as solvents, e.g. methanol, ethanol, and butanol.

The heating of the mixture is performed at a temperature ranging from 200° C. to 230° C., specifically ranging from 210° C. to 225° C., specifically ranging from 215° C. to 225° C. more specifically at a temperature of about 220° C.

According to a preferred embodiment, the heating is a sintering method, i.e heating forskolin and cyclodextrin without melting said components to the point of liquefaction. The applicable sintering temperature can be determined by the skilled person without undue burden.

Forskolin has a melting point ranging from 230 to 232° C., therefore the upper limit of the heating procedure is at about 230° C.

Cyclodextrins have melting points ranging from 250-290° C. depending on the type of cyclodextrin. As examples, the melting point of γ-cyclodextrin is about 267° C., the melting point of ß-cyclodextrin is about 260° C., the melting point of HP-ß-cyclodextrin is about 250° C., and the melting point of HP-γ-cyclodextrin is about 267° C.

The inclusion complex of the invention can be used for preparing a pharmaceutical composition. Said inclusion complex is highly advantageous because currently available forskolin cyclodextrin complexes have a maximum occupancy of about 2% or less, whereas the present complex has a forskolin occupancy of ≥2.5%, preferably ≥3%, preferably ≥3.5%, more preferably ≥4% and can be provided as medical grade preparation.

According to the invention there is provided an inclusion complex comprising forskolin and γ-cyclodextrin in a weight ratio of 1:0.2 to 1:4 (w/w), wherein forskolin and γ-cyclodextrin are comprised as an aqueous soluble complex.

In an embodiment of the invention there is provided an inclusion complex comprising forskolin and γ-cyclodextrin in a weight ratio of 1:0.3, 1:0.4, 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3, 3, 1:3.4, 1:3.5, 1:3.6, 1:3.7, 1:3.8, 1:3.9, or 1:4 (w/w).

In a specific embodiment of the invention there is provided an inclusion complex comprising forskolin and HP-γ-cyclodextrin in a weight ratio of 1:0.3, 1:0.4, 1:0.5, 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3, 3, 1:3.4, 1:3.5, 1:3.6, 1:3.7, 1:3.8, 1:3.9, or 1:4.

The forskolin cyclodextrin complex can be used for any dietary or medical purpose wherein soluble forskolin is applicable.

The specific dose of a complex administered according to this invention to obtain therapeutic or prophylactic effects will, of course, be determined by the particular circumstances surrounding the case, including, for example, the route of administration, the age, weight and response of the individual patient, the condition being treated and the severity of the patient's symptoms.

In general, the complex containing the compound forskolin as active agent of the invention is most desirably administered at a concentration that will generally afford effective results without causing any serious side effects and can be administered either as a single unit dose, or if desired, the dosage may be divided into convenient subunits administered at suitable times throughout the day.

The term "composition" as used herein specifically comprises the forskolin cyclodextrin inclusion complex of the invention, optionally together with other excipients or agents.

The composition can be provided in a variety of systemic and topical formulations. Systemic or topical formulations containing the inclusion complex of the invention are selected from the group of oral, intrabuccal, intrapulmonary, rectal, intrauterine, intradermal, topical, dermal, parenteral, intratumor, intracranial, intrapulmonary, buccal, sublingual, nasal, subcutaneous, intravascular, intrathecal, inhalable, respirable, intraarticular, intracavitary, implantable, transdermal, iontophoretic, intraocular, ophthalmic, vaginal, optical, intravenous, intramuscular, intraglandular, intraorgan, intralymphatic, slow release and enteric coating formulations. The actual preparation and compounding of these different formulations is known in the art and need not be detailed here. The composition may be administered once or several times a day.

Formulations suitable for respiratory, nasal, intrapulmonary, and inhalation administration are preferred, as are topical, oral and parenteral formulations. In general, the formulations are prepared by uniformly and intimately bringing forskolin presented as inclusion complex into association with a liquid carrier, a finely divided solid carrier, or both, and then, if necessary, shaping the product into desired formulations.

Compositions suitable for oral administration may be presented in discrete units, such as capsules, cachets, lozenges, or tablets, each containing the composition as a powder or granules; as a solution or a suspension in an aqueous or non-aqueous liquid; or as an oil-in-water or water-in-oil emulsion.

Compositions suitable for parenteral administration comprise sterile aqueous and non-aqueous injection solutions of the active compound, which preparations are preferably isotonic with the blood of the recipient. These preparations may contain anti-oxidants, buffers, bacteriostatic agents and solutes which render the compositions isotonic with the blood of the recipient. Aqueous and non-aqueous sterile suspensions may include suspending agents and thickening agents. The compositions may be presented in unit-dose or multi-dose containers, for example sealed ampoules and vials, and may be stored in a freeze-dried or lyophilized condition requiring only the addition of the sterile liquid carrier, for example, saline or water-for-injection immediately prior to use.

Nasal and instillable formulations comprise purified aqueous solutions of the composition with preservative agents and isotonic agents. Such formulations are preferably adjusted to a pH and isotonic state compatible with the nasal mucous membranes.

The composition disclosed according to the invention may be administered into the respiratory system either by inhalation, respiration, nasal administration or intrapulmonary instillation (into the lungs) of a subject by any suitable means, and are preferably administered by generating an aerosol or spray comprised of powdered or liquid nasal, intrapulmonary, respirable or inhalable particles. The respirable or inhalable particles comprising the active compound are inhaled by the subject, e.g. by inhalation or by nasal administration or by instillation into the respiratory tract or the lung itself. The formulation may comprise respirable or inhalable liquid or solid particles of the active compound that, in accordance with the present invention, include respirable or inhalable particles of a size sufficiently small to pass through the mouth and larynx upon inhalation and continue into the bronchi and alveoli of the lungs. In general, particles ranging from about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 and 2 to about 4, 4.5, 5, 5.5, 6, 6.5, 7, 7.5, 8, 8.5, 9, 9.5, 10 microns in diameter. More particularly, about 0.5 to less than about 5 µm in diameter, are respirable or inhalable. Particles of non-respirable size which are included in an aerosol or spray tend to deposit in the throat and be swallowed. The quantity of non-respirable particles in the aerosol is, thus, preferably minimized. For nasal administration or intrapulmonary instillation, a particle size in the range of about 8, about 10, about 20, about 25 to about 35, about 50, about 100, about 150, about 250, about 500 µm in diameter is preferred to ensure retention in the nasal cavity or for instillation and direct deposition into the lung. Liquid formulations may be squirted into the respiratory tract or nose and the lung, particularly when administered to newborns and infants.

Aerosols of liquid particles comprising the active compound may be produced by any suitable means, such as with a nebulizer. Nebulizers are commercially available devices which transform solutions or suspensions of the active ingredient into a therapeutic aerosol mist either by means of acceleration of a compressed gas, typically air or oxygen. Suitable compositions for use in nebulizer consist of the active ingredient in liquid carrier, the active ingredient comprising up to 40% w/w composition, but preferably less than 20% w/w carrier being typically water or a dilute aqueous alcoholic solution, preferably made isotonic with body fluids by the addition of, for example sodium chloride. Optional additives include preservatives if the composition is not prepared sterile, for example, methyl hydroxybenzoate, anti-oxidants, flavoring agents, volatile oils, buffering agents and surfactants. Aerosols of solid particles comprising the active compound may likewise be produced with any sold particulate medicament aerosol generator. Aerosol generators for administering solid particulate medicament, product particles which are respirable, as explained above, and generate a volume of aerosol containing a predetermined metered dose of a medicament at a rate suitable for human administration. Examples of such aerosol generators include metered dose inhalers and insufflators.

In one embodiment, the delivery device comprises a dry powder inhalator (DPI) that delivers single or multiple doses of the composition. The single dose inhalator may be provided as a disposable kit which is sterilely preloaded with enough formulation for one application. The inhalator may be provided as a pressurized inhalator, and the formulation in a piercable or openable capsule or cartridge.

The term "pharmaceutically acceptable" means approved by a regulatory agency of the Federal or a state government or listed in the U.S.

The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration.

The amount of the active drug in the inventive composition can be selected by any skilled person.

The term "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

Forskolin is well known to be an unspecific cAMP activating agent. The complex of the invention can be used for treating any disease or disorder that can be treated with forskolin. Such disorders may be, but are not limited to, neurodegenerative diseases, Alzheimer disease, motoric dysfunctions, acute and chronic heart diseases, pulmonary diseases, like asthma, cystic fibrosis, vascular diseases associated with cystic fibrosis, bronchitis, chronic obstructive pulmonary disease (COPD), adipositas, fibrotic alterations like idiopathic pulmonary fibrosis, post-traumatic pulmonary fibrosis and Broncho-pulmonary dysplasia in preterm and term newborns, post toxic liver diseases like VOD or liver cirrhosis, peripheral circulation disorders including Raynaud's disease and sklerodermia.

The present invention is further illustrated by the following examples without being limited thereto.

EXAMPLES

Example 1: Synthesis of Forskolin/Cyclodextrin Complex

Summary

Forskolin, a representative of the chemical group of diterpenes, is a largely water-insoluble plant constituent of *Plectranthus barbatus* (*Coleus forskolii*). Forskolin acts as adenylyl cyclase activator with a half-maximal effective concentration of about 10 µmol/l. Since the substance is largely water-insoluble, forskolin is dissolved in DMSO for use in assays. In order to avoid side effects of the solvent, forskolin is complexed with cyclodextrin in the present study and the thereby acquired novel properties such as solubility in water are defined. Lastly, the adenylyl cyclase activity is checked.

Complexing highly improves the solubility in water: 100 mg forskolin cyclodextrin complex (forskolin CD) is readily soluble in 2 ml of water, which is equivalent to 50 g per liter. As a result, approximately 1.2 g/L (and more) of forskolin can be dissolved in water (0.12%), which is approximately 120 times the solubility of native forskolin (only 0.001%).

In conventional inclusion methods, forskolin is predominantly complexed in aqueous media (Majeed M, Kumar A, Nagabuhushanam K, Prakash S. Process for preparing water soluble diterpenes and their applications. U.S. Pat. No. 6,960,300 B2, 2005). The herein described method leads to a maximum of 0.7% weight percent (w/w) of soluble forskolin in HP-γ-CD. Due to the novel forskolin sintering process developed here, occupancy levels of up to 4% (w/w) were achieved.

Use of the newly developed forskolin-CD complex for the stimulation of adenylyl cyclase shows a comparable potential as free forskolin, which is pre-dissolved in DMSO. One essential factor is the total concentration of forskolin in the reaction solution, not the choice of solvents or cyclodextrins (as a complexing agent for forskolin). There was no significant difference in the activation of adenylyl cyclase between forskolin dissolved in DMSO and water soluble forskolin with cyclodextrin.

Forskolin CD complexes are highly soluble in water and a comparable activation potential on the adenylyl cyclase could be determined: The forskolin-CD complex activates the enzyme to the same extent as forskolin dissolved in DMSO.

Herein, the occupancy of CD molecules was optimized and the corresponding manufacturing process was developed. While conventional methods show a 0.5-1.5% complexation of cyclodextrin, we could develop a method for forskolin and hydroxypropyl-γ-cyclodextrin which is able to reach 4% (w/w —up to a maximum of 4.7%) occupancy. This corresponds to a molecular occupancy of more than 15% and thus "saves" 2/3 of cyclodextrin. In the process cyclodextrins were sintered with forskolin at about 210-220° C.

FIG. 1 shows the structure of forskolin and binding sites to the C1 and C2 domain of adenylyl cyclase. The two OH-groups (marked in red) are essential for binding and must not be derivatized for these applications.

Material and Methods

Cyclodextrin (CD): Hydroxypropyl-γ-CD from Fluka 56334. Since hydroxypropyl derivatives are also permitted in the pharmaceutical field, these derivatives were also used. Furthermore, HP-γ-CD was purchased from Ashland (Wacker Chemie): trade name "Cavasol", batch: A1603A0012. RAMEB-CD is from Cyclolab R&D Ltd. Hungary, batch: CYL-4152.

Forskolin: an enriched extract (presumably CO2 extraction) from Sabinsa (www.sabinsaeuroope.com) Lot. C30698, with a content of 95% forskolin was used, which had been purified to over 98.5% in the course of the present project. Henceforth, the GMP quality of forskolin from MercaChem (batch: MAMA07-024-5, >99.7% HPLC) was used.

Calibration of Forskolin

For the first assessment of forskolin in various media, calibration was carried out through HPLC.

The following parameters were set for HPLC:
Mobile phase: acetonitrile:water=65:35 (v/v)
Stationary phase: polygosil 10C18, 250×4 mm
Detection: UV/VIS, 208 nm
Flow rate: 0.6 mL/min
Weighed portion of forskolin in the mobile phase: 0.05 mg/mL, 0.1 mg/mL, 0.5 mg/mL, 1.0 mg/mL.

Figure 2:
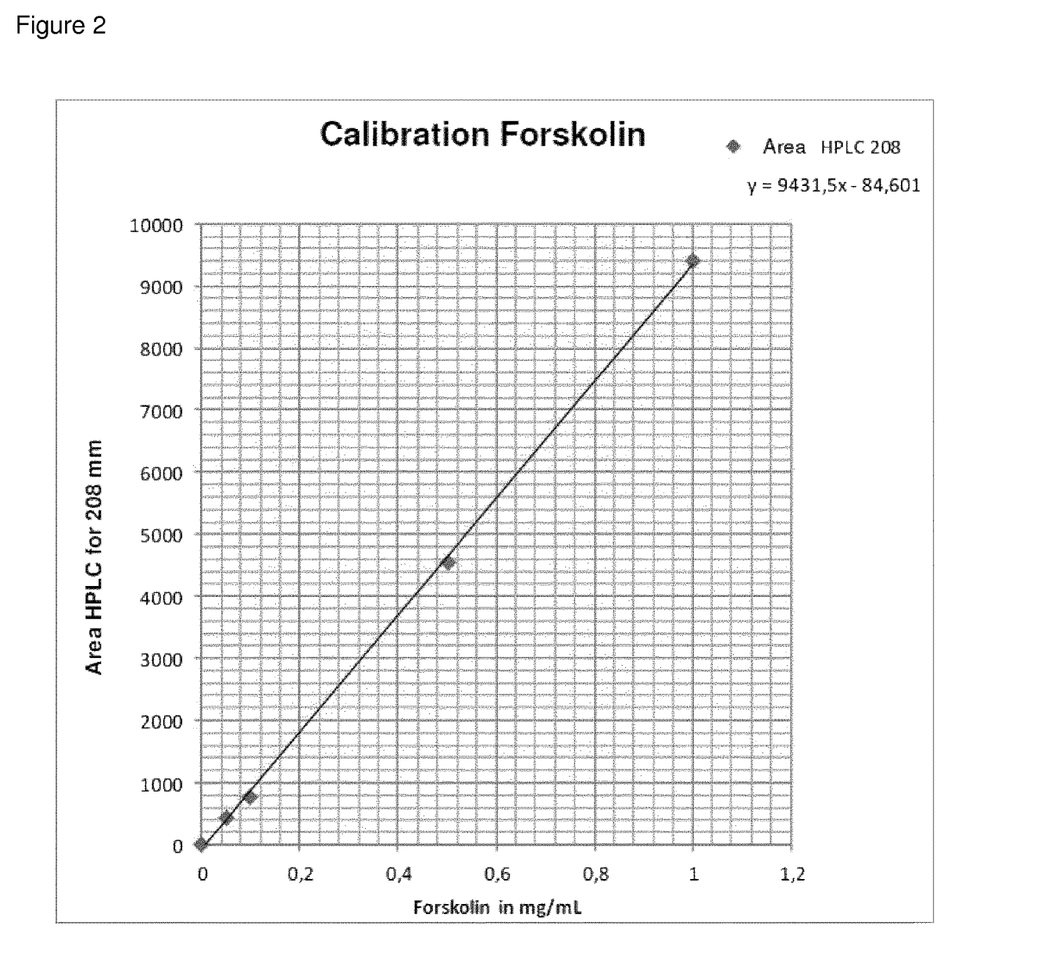
FIG. 2: Calibration of forskolin: y=9431x−84 (approximate).

The calibration curve is shown in FIG. 2: Calibration of forskolin: y=9431, x−84. It was constantly corrected and approximated due to the improvement of the forskolin source material, for example by generating higher purity, or the new quality of MercaChem.

Complexation of Forskolin with Cyclodextrins-Sintering Process

During sintering, powder or fine-grained materials were heated at temperatures below the melting temperature of the main components forskolin and cyclodextrin. The melting point of forskolin is at about 230° C., the melting point or decomposition point of the cyclodextrins is at about 260° C. If the mixture forskolin-CD was not heated above 220° C., the components were retained. Temperatures above 230° C. gave the matrix a brownish color indicating material changes.

A series of preliminary experiments showed that underivatized alpha- and beta-CDs complex exhibited smaller amounts of forskolin (<0.1%) whereas larger amounts of forskolin can be complexed with gamma-CD (>2%). The solubility of forskolin was optimized with HP-γ-CD.

80 mg HP-γ-CD+60 mg forskolin were mixed at a dry stage,
100 µl of water were added and mixed until a pasty mixture was received,
then 50 µl of 2-propanol were added,
the mixture was then sintered in a porcelain seal for about 20 minutes at approximately 210-220° C.,
3 ml water were added to the powder and stirred for about 10 minutes and left to stand for about 2 hours,
subsequently, the mixture was filtered (0.45 µm, Teflon filter),
the filtrate was dried in rotavapor and the amount of CD-forskolin complex) was determined by HPLC.

According to the calibration, the content of forskolin with 3-4 mg per 100 mg of forskolin-CD complex is to be indicated as follows: 3-4% (weight/weight) of the forskolin cyclodextrin complex (forskolin CD).

100 mg of forskolin CD was readily soluble in 2 ml of water, which is equivalent to 50 g per liter. Maximum solubility may even be higher.

Converted for forskolin, this corresponds to 1.2 g/L (0.12%), which corresponds approximately to a 120-fold solubility of native forskolin (water solubility of the native forskolin: 0.001%).

Analytics

The forskolin CD complex was very readily soluble in water. The content of forskolin was determined by HPLC, the parameters were described above.

The CD molecules, which are hydrophilic on the outside, were directly present in the elution profile after the injection peak (column is doped with an octadecyl phase, C18 reversed phase). Forskolin showed a retention time of 8 minutes.

18 mg of forskolin-CD complex was dissolved in 1.8 ml of mobile solvent=10 mg/ml. 20 µL were applied to the HPLC column.

Results

Complexation of Forskolin with CD Through the Sintering Process

According to the calibration, the content of forskolin should be indicated with a maximum of 4.7 mg per 100 mg forskolin-CD complex.

The maximum solubility of the forskolin-CD complex has not yet been determined since large quantities of material are required. Once the final product is received, the maximum solubility will be determined. However, 100 mg, up to 500 mg of forskolin-CD per mL of water were readily soluble, equivalent to 100 g (500 g) per liter.

Calculated for forskolin, this corresponds to 4.7 g/L (>0.47%), which corresponds approximately to the 500-fold solubility of forskolin (0.001%). Following method parameters have shown to be important:

The temperature range for sintering was shown to be highly effective between: 210° C.-220° C. If the temperature was below 205° C. or exceeded 220° C., it resulted in a smaller degree of occupancy as well as a more unstable complex.

Forskolin and CD must be stirred with water prior to sintering to form a paste and a small amount of alcohol, e.g. 2-propanol has to be added (Table 3).

Sintering—Novel Inclusion Process

Complexation of cyclodextrins was significantly increased by sintering cyclodextrins with forskolin at about 210° C. While conventional methods in liquid solvents have an average weight occupancy (MW) of averagely 1.7%+/−0.3 (SD), we were able to reach 3.7%+/−0.8 (SD) with the new sintering process The maximum occupancy was reached by means of the sintering process HP-CD, which resulted in 4.7% (w/w) and 18% (equimolecular), respectively.

Cell Culture Test—cAMP Assay

The method was performed at the Institute of Pharmacology, Medical University 10 of Vienna, Prof. Michael Freissmuth. The forskolin-CD complex was compared with an established method, where forskolin is dissolved and diluted in DMSO. The method has been described previously (Hussain F, et al., BMC Pharmacology 11 (2013), Suppl 2, A6) and is a test platform for the assessment of the chemical induction of stem cells.

Figure 3:
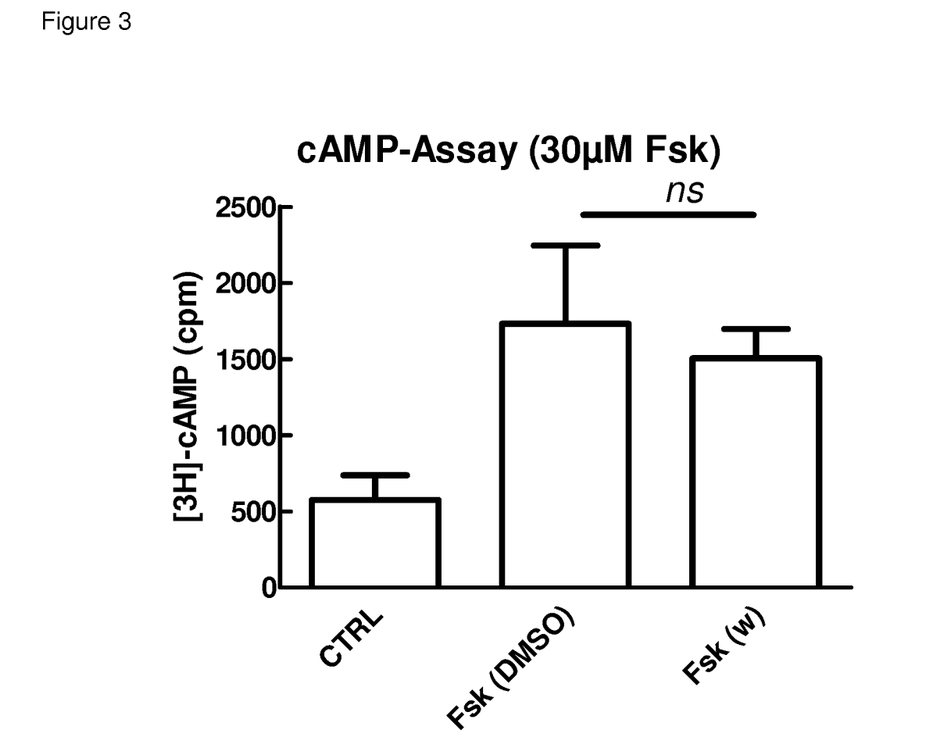
FIG. 3: cAMP assay for forskolin dissolved in DMSO and forskolin-CD complex, according to Hussain et al., 2013.

FIG. 3 shows the cAMP assay for forskolin dissolved in DMSO and forskolin-15 CD complex, according to Hussain et al., 2013.

Forskolin complexed with HP-gamma-CD, which in view of forskolin was present in the same concentration as forskolin dissolved in DMSO (concentration in medium=30 μmol/l), showed a comparable increase of the cytosolic cAMP (FIG. 3). Also, the lack of DMSO, which is considered to be a PDE inhibitor (see above), had no 20 effect on the results based on preliminary theoretical and practical aspects. The following batches were tested in aliquot molar concentrations as an activator of adenylyl cyclase:

TABLE 1

Verification of the activation potential for adenylyl cyclysis of various forskolin-CD complexes and comparison with native forskolin dissolved in DMSO. F-CD 116 (400 mg HP-γ-CD, 32 mg forskolin, 45° C. 1 h + 72 h RT); F-CD 118 (500 mg HP-γ-CD, 105 mg forskolin, 40° C. 3 h + 72 h RT), F-CD 119 (500 mg HP-β-CD, 105 mg forskolin, 40° C. 3 h + 72 h RT), F-CD 130 (80 mg HP-γ-CD, 60 mg forskolin, 165-210° C., 100 μL H₂O, 50 μL Propanol), F-CD 138 (80 mg HP-γ-CD, 60 mg forskolin, 140-220° C., 100 μL H₂O, 50 μL Propanol, citr.), F-CD 140 (240 mg HP-γ-CD, 180 mg forskolin, 200-228° C., 300 μL H2O, 150 μL Propanol, LYO).

| Batch | CD | Occupancy | Method of Production | Result |
|---|---|---|---|---|
| F-CD 116 | HP-γ-CD | 2.4 | Solvent incorporation | as FSK/DMSO |
| F-CD-118 | HP-γ-CD | 1.74 | Solvent incorporation | as FSK/DMSO |
| F-CD-119 | HP-γ-CD | 1.32 | Solvent incorporation | as FSK/DMSO |
| F-CD 130 | HP-γ-CD | 3.8 | Sintering process | as FSK/DMSO |
| F-CD 138 | HP-γ-CD | 4.15 | Sintering process | as FSK/DMSO |
| F-CD 140 | HP-γ-CD | 4.2 | Sintering process | as FSK/DMSO |

Figure 4:
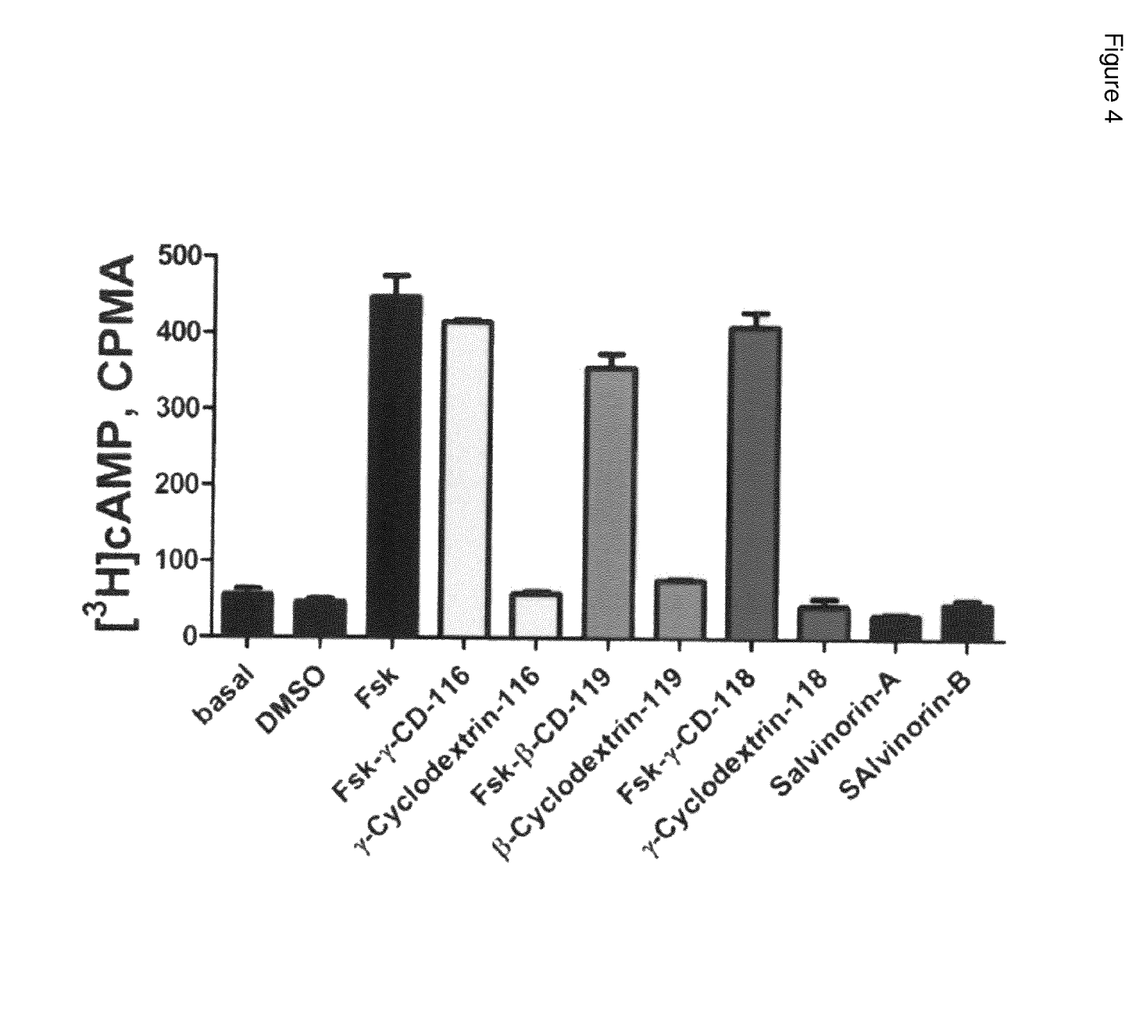
FIG. 4: cAMP assay for forskolin dissolved in DMSO and forskolin-CD complex. Comparison of γ-CD and ß-CD.

FIG. 4 shows a cAMP assay for forskolin dissolved in DMSO and forskolin-CD complex, according to Husain et al. (BMC Pharmacol. 11 (2013 (Suppl 2:A6. γ-CD and β-CD are compared herein. It is shown that there is no significant difference between forskolin dissolved in DMSO and forskolin γ-CD complex which proves that activity of forskolin complex bound in CD is not diminished, compared to forskolin dissolved in DMSO. Forskolin-β-CD activates the adenylyl cyclase slightly weaker. Inactive regarding the adenylyl cyclase are the control samples of pure cyclodextrins without forskolin, as well as the alternative diterpenes salvinorin A and salvinorin B.

CONCLUSION

The use of forskolin-CD inclusion complexes for the stimulation of adenylyl cyclase showed a comparable potential regarding the activation of adenylyl cyclase compared to free forskolin pre-dissolved in DMSO according to preliminary results.

The inner diameter of γ-CD is 9.5 Å (see Table 2), the width of the native forskolin molecule is about 8 Å (own calculation via the "ligand scout" program, Inte:ligand GmbH; length approx. 10.5 Å, widest point about 8 Å.

The narrow dimensions of the channel compared to forskolin and the inhomogeneous charge distribution within the forskolin molecule are presumably the cause for the low rate of occupancy of the CDs and the idleness of the occupancy reaction.

TABLE 2

Properties of natural cyclodextrins (CD) (8).

| Properties | α-CD | β-CD | γ-CD | δ-CD |
|---|---|---|---|---|
| Glucose units | 6 | 7 | 8 | 9 |
| Molar mass (G/Mol) | 972 | 1135 | 1297 | |
| Inner diameter (Å) | 5.7 | 7.8 | 9.5 | |
| Size of the hollow space (Å) | 7.8 | 7.8 | 7.8 | |
| Water solubility (g/L) RT | 145 | 18.5 | 232 | |

Example 2

Comparison of occupancy rate:

For comparison of the loading capacity of the present method, the method as described in US20050051483A1 was compared with the method as described above. The respective values had been calculated based on the data given in US20050051483A1.

According to US20050051483A1, forskolin was added to water containing HP-ß-CD, HP--γ--CD or RAMEB-CD in the dissolved state. Suspension was agitated at 75 rpm in an isothermal shaker for 60 hours at temperature −30° C. Resulting solution was filtered through 0.45 pm nylon filter and analyzed for the content of forskolin by HPLC (US20050051483A, examples 2, 3, 7).

TABLE 3 comparison of occupancy rate.

| | US20050051483A1 (w/w) | Inventive method (w/w) |
|---|---|---|
| β-CD | n.d. | 0.8 |
| HP-β-CD | 0.3 | 2.6 |
| 50% RAMEB-CD | 5.9 | 9 |
| HP-γ-CD | 0.7 | 3.7 |

It has thus been specifically shown by the inventors, that HP-ß-CD, RAMEB-CD, and HP--γ--CD show significantly increased occupancy rate.

The invention claimed is:

1. A method for preparing a forskolin cyclodextrin inclusion complex comprising the steps:
   a) mixing forskolin and cyclodextrin in a weight ratio of 1:0.5 to 1:4,
   b) adding water and solvent to form a mixture,
   c) heating said mixture at a temperature ranging from 180° C. to 230° C.,
   d) adding water to said mixture followed by mixing and allowing the mixture to precipitate,
   e) isolating the precipitate from the mixture and optionally drying the precipitate.

2. The method according to claim 1, wherein the cyclodextrin is selected from the group consisting of α cyclodextrin, hydroxypropyl-α cyclodextrin, ß-cyclodextrin, γ-cyclodextrin.

3. The method according to claim 1, wherein the cyclodextrin is selected from the group consisting of hydroxypropyl-ß-cyclodextrin, hydroxypropyl-γ-cyclodextrin and RAMEB-CD.

4. The method according to claim 1, wherein the heating temperature is 210° C. or 220° C.

5. The method according to claim 1, wherein the method is a method for producing a powdered inclusion complex of forskolin and HP-γ-cyclodextrin.

6. The method according to claim 1, wherein the solvent is an alcohol.

7. The method according to claim 1, wherein heat drying is carried out for about 1 to 30 minutes.

8. The method according to claim 1, wherein the precipitate is filtered.

9. The method according to claim 1, wherein the precipitate is dried at room temperature.

10. The method according to claim 1, wherein step c) comprises heating said mixture at a temperature ranging from 200 to 230° C.

11. The method according to claim 1, wherein step c) comprises heating said mixture at a temperature ranging from 210 to 220° C.

12. The method according to claim 11, wherein step c) comprises heating said mixture at a temperature about 220° C.

13. The method according to claim 6, wherein the alcohol is 2-propanol.

14. The method according to claim 8, wherein the precipitate is filtered by membrane filtration.

* * * * *

UNITED STATES PATENT AND TRADEMARK OFFICE
CERTIFICATE OF CORRECTION

| | | |
|---|---|---|
| PATENT NO. | : 11,234,957 B2 | |
| APPLICATION NO. | : 16/476337 | |
| DATED | : February 1, 2022 | |
| INVENTOR(S) | : Kubin | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 231 days.

Signed and Sealed this
Seventh Day of February, 2023

Katherine Kelly Vidal
*Director of the United States Patent and Trademark Office*